United States Patent [19]

Norman et al.

[11] Patent Number: 5,380,738

[45] Date of Patent: Jan. 10, 1995

[54] 2-SUBSTITUTED OXAZOLES FURTHER SUBSTITUTED BY 4-FLUOROPHENYL AND 4-METHYLSULFONYLPHENYL AS ANTIINFLAMMATORY AGENTS

[75] Inventors: Bryan H. Norman; Len F. Lee, both of St. Charles; Jaime L. Masferrer, Ballwin; John J. Talley, St. Louis, all of Mo.

[73] Assignee: Monsanto Company, St. Louis, Mo.

[21] Appl. No.: 65,730

[22] Filed: May 21, 1993

[51] Int. Cl.⁶ .......................................... C07D 263/32
[52] U.S. Cl. ................................. 514/374; 548/235; 548/236
[58] Field of Search ................ 548/235, 236; 514/374

[56] References Cited

U.S. PATENT DOCUMENTS

| | | | |
|---|---|---|---|
| 3,578,671 | 5/1971 | Brown | 548/235 |
| 3,644,399 | 2/1972 | Brown | |
| 3,743,656 | 7/1973 | Brown | |
| 3,895,024 | 7/1975 | Mattalia | 548/229 |
| 4,001,228 | 1/1977 | Mattalia | 548/236 |
| 4,020,082 | 4/1977 | Marchetti | 548/235 |
| 4,051,250 | 9/1977 | Dahm | |
| 4,143,047 | 3/1979 | Harrison | 548/229 |
| 4,489,084 | 12/1984 | Haviv | 548/233 |
| 4,532,253 | 7/1985 | Mughal | 514/374 |
| 4,590,205 | 5/1986 | Haber | |
| 4,632,930 | 12/1986 | Carini | 548/235 |
| 4,774,253 | 9/1988 | Machin et al. | 514/374 |
| 4,775,687 | 10/1988 | Meguro et al. | 548/235 |
| 4,791,124 | 12/1988 | Lutomski et al. | 514/374 |
| 4,990,647 | 2/1991 | Himmler | |
| 5,061,705 | 10/1991 | Wuest | 548/373 |
| 5,206,255 | 4/1993 | Ubasawa et al. | 514/374 |
| 5,262,540 | 11/1993 | Meanwell et al. | 548/235 |

FOREIGN PATENT DOCUMENTS 418845 9/1990 European Pat. Off.
517591 12/1992 European Pat. Off. ............ 514/374

OTHER PUBLICATIONS

E.P. 418845 Sep. 19, 1990 Pyrazole derivatives, processes for preparation thereof & pharmaceutical composition comprising the same.
Derwent Abstract No. 91-067958/10 (1991).
Derwent Abstract No. 41925U-B (1973).
Derwent Abstract No. 26458 E/14 (1982).
Derwent Abstract 90-370247/50 (1990).
Masferrer, et al. in Proc. Natl. Acad. Sci. USA, vol. 89, pp. 39173921 (May 1992) entitled "Endogenous glucocorticoids regulate an inducible cyclooxygenae enzyme".
T. Hla and K. Neilson Proc. Natl. Acad. Sci. USA, vol. 89, pp. 7384–7388, (Aug. 1992) entitled "Human cyclooxygenase-2 cDNA".
Raz, A., et al., Proc. Natl. Acad. Sci. USA 86, 1657–1661, 1989.
Meanwell et al. I Jour. Med. Chem. vol. 35 pp. 3483–3497 (1992).
Meanwell et al. II Jour. Med. Chem. vol. 35 pp. 3498–3512 (1992).
Aldous et al., J. Org. Chem. vol. 25, pp. 1151–1154 (1960).

Primary Examiner—Donald G. Daus
Attorney, Agent, or Firm—Joan Thierstein; Joseph W. Bulock

[57] ABSTRACT

2-Substituted-4-(4-fluorophenyl)-5-(4-(methylsulfonyl)-phenyl)oxazoles or 2-substituted-5-(4-fluorophenyl)-4-(4-(methylsulfonyl)phenyl)oxazoles and derivatives thereof are found to posses significant antiinflammatory activity, especially useful for the treatment of arthritis without deleterious side effects.

21 Claims, No Drawings

5,380,738

2-SUBSTITUTED OXAZOLES FURTHER SUBSTITUTED BY 4-FLUOROPHENYL AND 4-METHYLSULFONYLPHENYL AS ANTIINFLAMMATORY AGENTS

BACKGROUND OF THE INVENTION

The present invention relates to 4,5-oxazole derivatives and analogs thereof, pharmaceutical compositions containing them and methods of using them to treat inflammation and/or pain in mammals. More particularly, this invention relates to selected 2-substituted-4-(4-fluorophenyl)-5-(4-(methylsulfonyl)phenyl)oxazoles or 2-substituted-5-(4-fluorophenyl)-4-(4-(methylsulfonyl)phenyl)oxazoles having antiinflammatory and/or analgesic activity without erosion of the stomach.

2,3-Diaryl-5-halo thiophenes are disclosed in U.S. Pat. No. 4,590,205 as analgesic or antiinflammatory agents. More particularly, 2,3-diaryl-5-bromo thiophenes are disclosed in U.S. Pat. No. 4,820,827 as having unexpected antiinflammatory and prostaglandin synthetase inhibitory activity for use in the treatment of inflammation and dysmenorrhea. Copending application U.S. Ser. No. 08/004,822 discloses 4-(4-fluorophenyl)-5-(4-methylsulfonylphenyl)thiophene and its 2-substituted bromo analog among its preferred compounds for antiinflammatory activity.

WO/91/19708 discloses thiophenes having various 5-substituents, as well as, 2,3-substitutions having antiinflammatory activity.

U.S. Pat. No. 3,743,656 and U.S. Pat. No. 3,644,399, which is the parent of U.S. Pat. No. 3,743,656, disclose more generically both thiophene and furane derivatives having antiinflammatory activity.

Preparation of a wide-variety of asymmetric biaryl compounds including substituted thiophene, furane and pyrrol rings is disclosed in U.S. Pat. No. 4,990,647 having a suggested utility as precursors for brighteners, pharmaceuticals, plant protection active compounds and liquid crystal materials.

Pyrazole derivatives having antiinflammatory activity are disclosed in European Patent Application Number 90117983.8.

Agents for the treatment of hypertension are disclosed as alkyl-arylimidazole, thiazole and oxazole derivatives in U.S. Pat. No. 4,632,930.

More specifically, U.S. Pat. No. 3,578,671 discloses oxazoles substituted in the 2-position by a saturated or unsaturated aliphatic acid and having 4 and 5 substituents, including phenyl which may be further substituted. French 2156486 of Derwent Abstract No. 41925U-B and U.S. Pat. No. 4,051,250 both generically disclose compounds including 2-oxazolylmercaptoalkanoic acid (esters, amides or cyano derivatives) ring systems having 4,5-diaryl groups which are phenyls both unsubstituted or substituted by a wide variety of substituents and having antiphlogistic, analgesic and antipyretic activity, particularly useful for treating arthritis.

Diarylheterocycles are disclosed in CA114(5):42807w for use as drugs including use against rheumatic and arthritic diseases.

Other related disclosures include U.S. Pat. No. 4,001,228 for antiaggregating activity and U.S. Pat. No. 3,895,024 for intermediates in the production of antiinflammatory agents.

U.S. Pat. No. 4,489,084 describes oxazolyl (or thiazolyl) hydrazinoalkyl nitrile compounds having including two phenyl substituents which phenyls are also further substituted for use as antiinflammatory agents. U.S. Pat. No. 4,143,047 entitled "2-Sulfinyl and 2Sulfonyl Oxazoles" discloses such compounds as reactants to make 2-acylamino oxazole derivatives having antiallergic activity.

Additionally, German Patent No. 3030661 described in Derwent Abstract No. 26458 E/14 provides heteroarylpropargyl ethers as synergists in pesticides, EP 402-246A described in Derwent Abstract 90-370247/50 provides azolyl-substituted alkoxy-acrylate derivatives for use as fungicides and Japanese Patent No. 3014-562 A described in Derwent Abstract No. 91-067958/10 provides alkylene diamine derivatives useful as glutamic acid blockers.

The above references, that disclose antiinflammatory activity, show continuing efforts to find a safe and effective antiinflammatory agent. The novel oxazoles disclosed herein are such safe and also effective antiinflammatory agents furthering such efforts.

The invention compounds are found to show usefulness in vivo as antiinflammatory agents, particularly as antiarthritic agents without ulcerogenic side effects.

SUMMARY OF THE INVENTION

This invention relates to novel compounds of the formula (I)

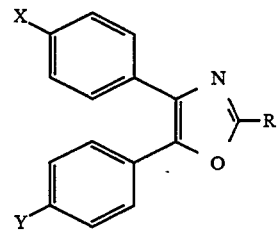

and a pharmaceutically acceptable salt thereof; wherein

X and Y are independently fluoro or methylsulfonyl; and

R is 1) hydrogen;

2) alkyl of from one to ten carbon atoms optionally substituted by hydroxy;

3) alkenyl of from two to ten carbon atoms optionally substituted by hydroxy;

4) alkynyl of from two to ten carbon atoms optionally substituted by hydroxy;

5) cycloalkyl of from 3 to 7 carbons;

6) cycloalkylalkyl wherein cycloalkyl is as defined above and alkyl is alkylenyl of from one to three carbons;

7) aryl which is phenyl, 2- or 3-thienyl or 1-, 2- or 3-naphthyl wherein the aryl is optionally substituted by alkoxy of from one to four carbon atoms or halo;

8) aralkyl wherein ar is aryl as defined above and alkyl is alkylenyl is of from one to three carbons;

9) diarylalkyl wherein aryl is as defined above and alkyl is alkylenyl of from one to four carbon atoms;

10) $QR^1$ wherein Q is alkylenyl of from one to four carbon atoms and $R^1$ is $COR^2$ wherein $R^2$ is 1) $OR^3$ wherein $R^3$ is hydrogen or alkyl of from one to four carbon atoms or 2) $NR^4R^5$ wherein $R^4$ and $R^5$ are independently hydrogen and alkyl of from one to four carbon atoms;

The present invention is also a pharmaceutical composition for the treatment of inflammation comprising an antiinflammatory amount of a compound of the formula I together with a pharmaceutically acceptable carrier.

The present invention is also a method of treating a human suffering from an inflammatory disease which comprises administering a compound of the formula of I in unit dosage form.

DETAILED DESCRIPTION

"Lower alkyl of from one to four" or "ten carbons" in the present invention means methyl, ethyl, propyl, butyl or further pentyl, hexyl, heptyl or the like and isomers thereof respectively.

"Halogen is chloro, fluoro or bromo.

"Lower alkenyl of from two to ten carbons" means ethenyl, 1- or 2-propenyl, 1-, 2- or 3-butenyl and the like and isomers thereof.

"Lower alkynyl of from two to ten carbons" means ethynyl, 1- or 1-propynyl, 1-, 2- or 3-butynyl and the like and isomers thereof.

"Alkylenyl of from one to three" or "to four" is a bridging alkyl chain, i.e. having two open bonds, such as methylenyl, ethylenyl, propylenyl or further butylenyl and isomers thereof.

The compounds of the present invention may contain asymmetric carbon atoms, and, therefore, the instant invention may also include the individual diastereomers and enantiomers, which may be prepared or isolated by methods known to those skilled in the art.

In other words, any resulting racemate can be resolved into the optical antipodes by known methods, for example, by separation of the diastereomeric salts thereof, with an optically active acid, and liberating the optically active amine compound by treatment with a base. Racemic compounds of the present invention can thus be resolved into their optical antipodes e.g., by fractional crystallization of d- or l-(tartrates, mandelates, or camphorsulfonate) salts.

Additional methods for resolving optical isomers, known to those skilled in the art may be used, for example, those discussed by J. Jaques, A. Collet, and S. Wilen in *Enantiomers, Racemates, and Resolutions,* John Wiley and Sons, New York (1981).

The compounds I of the invention may preferably be pharmaceutically acceptable salts. Such salts may be basic or acid salts, for example, sodium, potassium, ammonium, calcium, magnesium, acetate, adipate, alginate, citrate, aspartate, benzoate, benzenesulfonate, bisulfate, butyrate, camphorate, camphorate, camphorsulphonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate, or phosphate, sulfate, chloride, carbonate and the like. The compounds of the invention are acids, acid derivatives, or when possible basic amines. The basic amines may be used to make acid addition salts of pharmaceutically acceptable weak inorganic or organic acids. These may include such inorganic acids as hydrochloric acid, sulphuric acid and phosphoric acid and such organic acids as oxalic acid, maleic acid, succinic acid and citric acid.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

Compounds of the present invention also are meant to include, where possible, hydrated species.

The preferred compounds of the present invention are the compounds of Formula I wherein R is n-propyl, 3-methoxybenzyl, phenyl or diphenylmethyl.

The more preferred compound is of the Formula I wherein R is phenyl.

General Procedure for the preparation of 4,5-(4-fluorophenyl)[(4-methylsulfonyl)phenyl]oxazole and Derivatives of the Formula I The procedures utilized in the preparation of the compounds of the formula I of the present invention are essentially that shown by the following Schemes 1 and 2.

Scheme 1

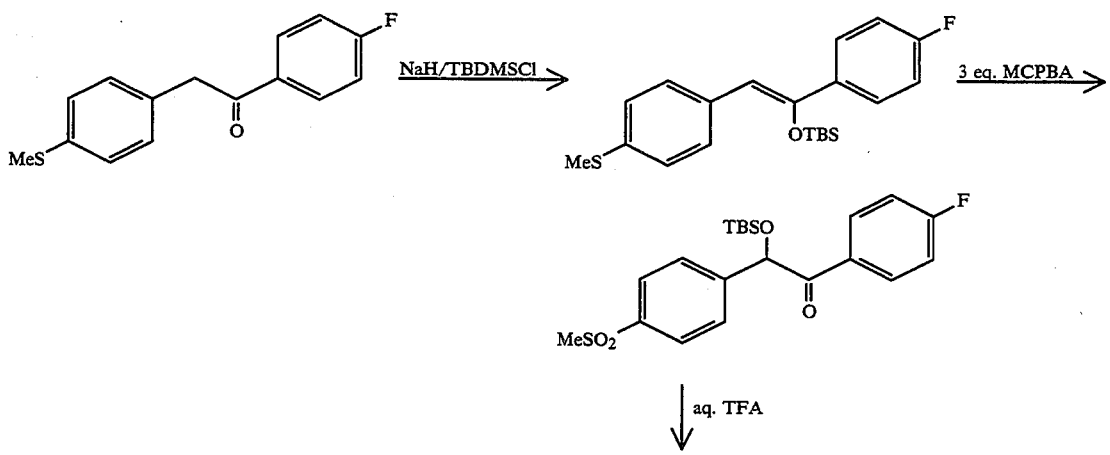

-continued
Scheme 1

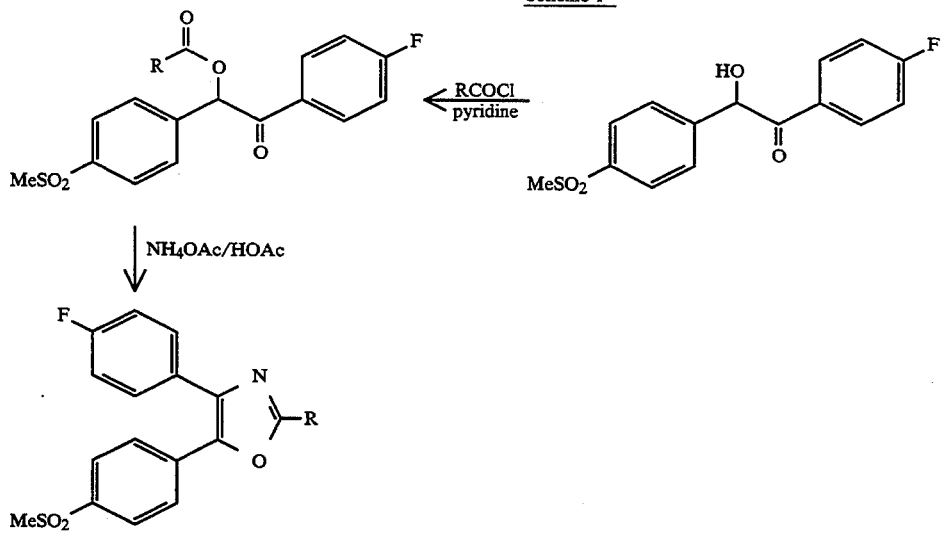

Scheme 2

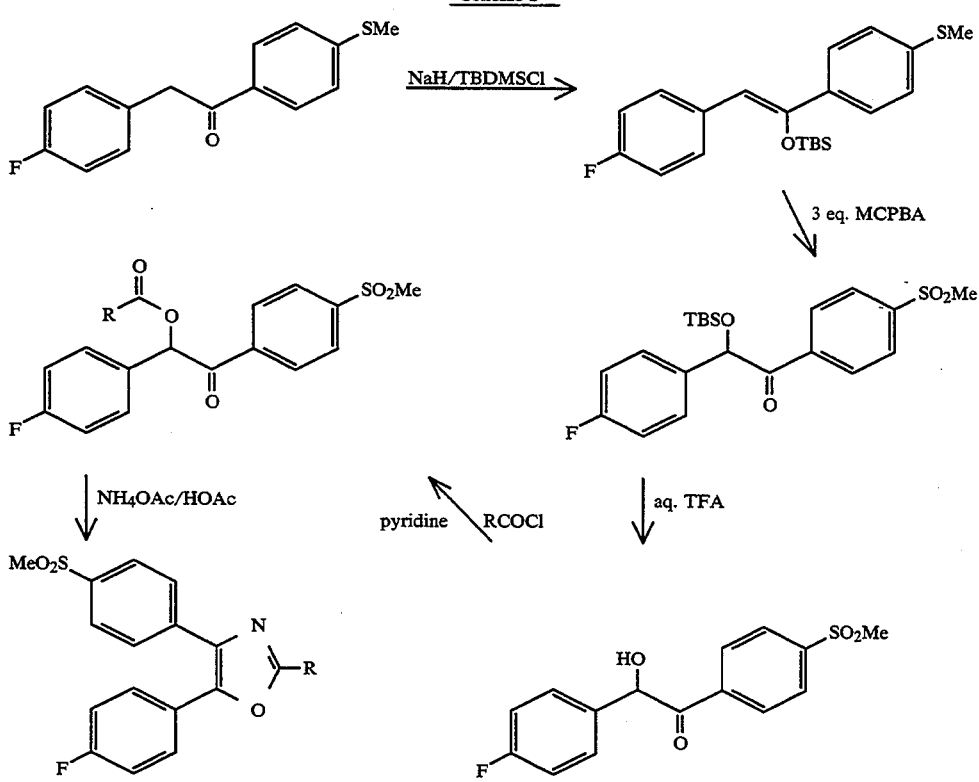

TBDMSCl is tert-butyl-dimethylsilyl chloride MCPBA is meta-chlorperoxybenzoic acid.

Generally, the above process is carried out as follows:

The synthesis of oxazoles of general formula I (schemes 1 and 2) begins with either 1-(4-fluorophenyl)-2-[4-(methylthio)phenyl]ethanone or 2-(4-fluorophenyl)1-[4-methylthio)phenyl]ethanone previously described in U.S. Pat. No. 3,647,858. Preparation of the silyl enol ether of this material is followed by oxidation with m-chloroperbenzoic acid to give the appropriate silylated benzoin. Desilylation of this material is achieved using aqueous trifluoroacetic acid to give the desired benzoin. Reaction of the benzoin with the appropriate acid chloride in the presence of pyridine gives the benzoin esters which may be converted to the oxazole upon treatment with ammonium acetate in refluxing acetic acid.

The following examples are not meant to limiting.

EXAMPLE 1

4-(4-FLUOROPHENYL)-2-HYDROXY-2-(2-PHENYL)ETHYL-5-(4-(METHYLSULFONYL)-PHENYL)OXAZOLE

Part 1

Preparation of 1-(4-Fluorophenyl)-2-Hydroxy-2-(Methylsulfonyl)Phenyl)Ethanone

A suspension of 2.03 g sodium hydride in 125 mL THF is stirred at 0° C. under a nitrogen atmosphere as a solution containing 20.0 g of 1-(4-fluorophenyl)-2-[4-(methylthio)phenyl]ethanone, as prepared in U.S. Pat. No. 3,647,858, in 100 mL of THF is added dropwise over 30 min. The reaction is allowed to warm to 25° C. for 18 h. The reaction is quenched by pouring into aqueous sodium bicarbonate. The mixture is extracted with ethyl acetate and the combined organic extracts dried over sodium sulfate. Concentration in vacuo provides a yellow oil, which solidified on standing to give 27.9 g of the silyl enol ether. NMR spectra is consistent with the assigned structure. The silyl enol ether is used without further purification.

A solution containing 27.9 g of the silyl enol ether in 500 mL $CH_2Cl_2$ is cooled to 0° C. under a nitrogen atmosphere while being stirred mechanically. 77.1 g of m-chlorperoxybenzoic acid (technical grade, 50–60%) is added and the reaction is stirred at 0° C. for 2 h and allowed to warm to 25° C. over 1 h. The reaction mixture is washed with an aqueous solution of sodium metabisulfite, followed by aqueous sodium bicarbonate. The organic solution is dried over sodium sulfate and concentrated in vacuo to give 24.5 g of 1-(4-fluorophenyl)-2-tert-butyldimethylsilyloxy-2-[4-(methylsulfonyl)phenyl]ethanone. NMR spectra were consistent with the assigned structure. This material is used without further purification.

The benzoin silyl ether is dissolved in 100 mL of 90% aqueous trifluoroacetic acid and stirred at 25° C. for 18 h. The reaction is quenched by slowly pouring into saturated aqueous sodium bicarbonate solution. The product is extracted with ethyl acetate and the combined organic extracts are dried over sodium sulfate. Concentration in vacuo provided an oily solid, which is recrystallized from 50% ethyl acetate-isooctane to give 15.5 g of a crystalline white solid (mp 122–123° C.) whose structure is assigned as 1-(4-Fluorophenyl)-2-Hydroxy-2-(Methylsulfonyl)Phenyl)Ethanone on the basis of its spectral properties.

The isomeric benzoin, 2-(4-fluorophenyl)-2-hydroxy-1-(4-(methylsulfonyl)phenyl)ethanone, is prepared analogously from 2-(4-fluorophenyl)-1-[4-(methylthio)-phenylethanone.

Part 2
Preparation of 4-(4-fluorophenyl)-2-(2-phenylethyl)-5-(4-(methylsulfonyl)phenyl)oxazole.

A solution containing 5.00 g of 1-(4-fluorophenyl)-2-hydroxy-2-(4-(methylsulfonyl)phenyl)ethanone in 100 mL $CH_2Cl_2$ is stirred at 25° C. as 6.60 mL of pyridine is added, followed by 3.61 mL of hydrocinnamoyl chloride.

The reaction is stirred at 25° C. for 48 h, after which the organic solution is washed with 1N HCl, dried over sodium sulfate and concentrated in vacuo to give an oily solid. This material is recrystallized from 50% ethylacetate-isooctane to give 4.40 g of a beige crystalline solid (mp 152°–153.5° C.). NMR spectra are consistent with the assigned structure of 1-(4-fluorophenyl)-2-[4-(methylsulfonyl)phenyl]-2-(2-phenyl)propionyloxy ethanone. This material is dissolved in 100 mL of glacial acetic acid and 7.70 g of ammonium acetate is added. The reaction is heated to reflux with stirring for 1.5 h, after which it is cooled to room temperature and poured into 100 mL of water. The product is extracted with ethyl acetate and the combined organic extracts washed with aqueous sodium bicarbonate, dried over sodium sulfate and concentrated in vacuo to give an oily solid which is recrystallized from 50% ethyl acetate—isooctane to give 3.55 g of a white crystalline solid (mp 117°–118° C.) which is 4-(4-fluorophenyl)-2-(2-phenylethyl)-5-(4-(methylsulfonyl)phenyl)oxazole. NMR spectra is consistent with the assigned structure.

EXAMPLE 2

Using appropriate corresponding starting materials the following compounds are prepared in an analogous fashion:

Part 1) 4-(4-Fluorophenyl)-2-methyl-5-[4-(methylsulfonyl)phenyl]oxazole, mp 158°–159° C.

Part 2) 4-(4-Fluorophenyl)-5-[4-(methylsulfonyl)phenyl]-2-phenyloxazole, mp 204°–205° C.

Part 3) 2-Benzyl-4-(4-fluorophenyl)-5-(4-(methylsulfonyl)phenyloxazole, ms m/z 408 (M+H)+.

Part 4) 4-(4-fluorophenyl)-5-[4-(methylsulfonyl)phenyl]-2-(3-phenyl)propyloxazole, ms m/z.

Part 5) 4-(4-fluorophenyl)-5-[4-(methylsulfonyl)phenyl]-2-propyloxazole, ms m/z 436 (M+H)+.

Part 6) 2-(tert-butyl)-4-(4-fluorophenyl)-5-[4-(methylsulfonyl)phenyl]oxazole, mp 130°–131 ° C.

Part 7) 4-(4-fluorophenyl)-2-(4-methoxyphenyl)methyl-5-[4-(methylsulfonyl)phenyl]oxazole, mp 123°–124° C.

Part 8) 4-(4-fluorophenyl)-2-(3-methoxyphenyl)methyl-5-[4-(methylsulfonyl)phenyl]oxazole, ms m/z.

Part 9) 2-diphenylmethyl-4-(4-fluorophenyl)-5-[4-(methylsulfonyl)phenyl]oxazole, mp 155°–156 ° C.

Part 10) 4-(4-fluorophenyl)-5-[4-(methylsulfonyl)phenyl]oxazoleacetic acid, ethyl ester, mp 123°–124° C.

Part 11) 4-(4-fluorophenyl)-5-[4-(methylsulfonyl)phenyl]oxazolepropionic acid, methyl ester, ms m/z 404(M+H)+.

Part 12) 4-(4-fluorophenyl)-5-[4-(methylsulfonyl)phenyl]oxazolebutanoic acid, methyl ester, mp 89°–91° C.

Part 13) 5-(4-fluorophenyl)-2-methyl-4-[4-(methylsulfonyl)phenyl]oxazole ms $^{m/z}$ 332 (M+H)+.

Part 14) 5-(4-fluorophenyl)-4-[4-(methylsulfonyl)phenyl]-2-oxazolepropionic acid, methyl ester ms m/z 404 (M+H)+.

The following acids were prepared from their corresponding esters via alkaline hydrolysis using 1N sodium hydroxide in methanol and appropriate reaction conditions.

Part 15) 4-(4-fluorophenyl)-5-[4-(methylsulfonyl)phenyl]-2-oxazoleacetic acid mp 118°–120° C.

Part 16) 4-(4-fluorophenyl)-5-[4-(methylsulfonyl)phenyl]-2-oxazolepropionic acid ms m/z 390 (M+H) +.

Part 17) 4-(4-fluorophenyl)-5-[4-(methylsulfonyl)phenyl]-2-oxazolebutanoic acid. ms m/z 404 (M+H)+.

Part 18) 5-(4-fluorophenyl)-4-[4-(methylsulfonyl)phenyl]-2-oxazolepropanoic acid ms m/z 390 (M+H)+.

Part 19) 4-(4-fluorophenyl)-5-[4-(methylsulfonyl phenyl]-2-(3-hydroxy)propyloxazole is prepared by treating 4-(4-fluorophenyl)-5-[4-(methylsulfonyl)phenyl]-2-oxazolepropanoic acid, methyl ester with diisobutylaluminum hydride. NMR spectra are consistent with the assigned structure, mp 123°–124° C.

Part 20) 4-(4-fluorophenyl)-5-(4-(methylsulfonyl)-phenyl)-2-oxazolepropionic amide is prepared by treating 4-(4-fluorophenyl)-5-(4-(methylsulfonyl)phenyl)-2-oxazolepropionic acid, methyl ester with excess ammonia in methanol for 5 days, mp 193°–195° C.

Dosage Forms

The antiinflammatory agents of this invention can be administered to treat inflammation by any means that produces contact of the active agent with the agent's site of action in the body of a mammal, preferably human. These agents can be administered by any conventional means available for use in conjunction with pharmaceuticals, either as individual therapeutic agents or in a combination of therapeutic agents. The agents can be administered alone, but are generally administered with a pharmaceutical carrier selected on the basis of the chosen route of administration, preferably oral, and standard pharmaceutical practice.

Total daily dose administered to the mammal, preferably human, in single or divided doses may be in amounts, for example, from 0.1 to 100 milligrams per kilogram of body weight. Ordinarily 0.5 to 50, and preferable 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The amount of active ingredient that may be combined with the carrier materials to produce a single dosage form will vary depending upon the host treated and the particular mode of administration.

The dosage regimen to give relief from or ameliorate a disease condition (i.e., treatment) having inflammation as an element of the disease, such as arthritis, or protecting against the further inflammation (i.e., prophylaxis) with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetics and toxicology profiles of the particular compound employed, whether a drug delivery system is utilized and whether the compound is administered as part of a drug combination. Thus, the dosage regimen actually employed may vary widely and therefore deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings, if necessary.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutically acceptable carriers encompass all the foregoing and the like.

While the compounds of the invention can be administered as the sole active pharmaceutical agent, they can also be used in combination with one or more immunomodulators, antiviral agents or other antiinfective agents. For example, the compounds of the invention can be administered in combination with antihistamines or with other such agents known heretofore to be effective in combination with antiinflammatory agents. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be with in the scope and nature of the invention which are defined in the appended claims.

The examples herein can be repeated with similar success by substituting the generically or specifically described reactants and/or operating conditions of this invention for those used in the preceding examples.

Adjuvant-Induced Arthritis in Rats

The antiinflammatory utility of the compounds of the present invention is shown by an assay essentially performed in an animal model using a procedure recognized to show antiinflammatory activity. See Winter et al in "Carrageenan-induced Edema in Hind Paw of the Rat" Proc. Soc. Exp. Biol. Med., 111, 544, 1962.

The $IC_{50}$ shows the % decrease from control paw volume determined in this procedure and the data for a selected compound in this invention is summarized in Table 2.

TABLE 2

| | Rat Paw ED$_{40}$ mg/kg |
|---|---|
| Example 1 Part 2 | 5 |

What is claimed is:

1. A compound of the formula (I)

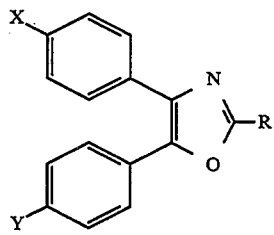

wherein
X and Y are independently fluoro or methylsulfonyl; and
R is
a) hydrogen;
b) alkyl of from one to ten carbon atoms optionally substituted by hydroxy;
c) alkenyl of from two to ten carbon atoms optionally substituted by hydroxy;
d) alkynyl of from two to ten carbon atoms optionally substituted by hydroxy;
e) cycloalkyl of from 3 to 7 carbons;
f) cycloalkylalkyl wherein cycloalkyl is as defined above and alkyl is of from one to three carbons;
g) aryl which is phenyl, thienyl or 1-, or 2-naphthyl wherein the aryl is optionally substituted by alkoxy of from one to four carbon atoms or halo;
h) aralkyl wherein ar is aryl as defined above and alkyl is of from one to three carbons;
i) diarylalkyl wherein aryl is as defined above and alkyl is of from one to four carbon atoms; or
j) QR$^1$ wherein Q is alkylenyl of from one to four carbon atoms and R$^1$ is COR$^2$ wherein R$^2$ is 1) OR$^3$ wherein R$^3$ is hydrogen or alkyl of from one to four carbon atoms or 2) NR$^4$R$^5$ wherein R$^4$ and R$^5$ are independently hydrogen and alkyl of from one to four carbon atoms;
or a pharmaceutically-acceptable salt thereof;
provided one of X and Y is methylsulfonyl.

2. A compound of claim 1 wherein X is F and Y is SO$_2$CH$_3$.

3. A compound of claim 1 wherein X is SO$_2$CH$_3$ and Y is F.

4. A compound of claim 1 wherein R is phenyl.

5. A compound of claim 1 wherein R is 3-methoxybenzyl, diphenylmethyl or benzyl.

6. A compound of claim 3 which is 5-(4-fluorophenyl)-2-methyl-4-[4-(methylsulfonyl)phenyl]oxazole, 5-(4-fluorophenyl)-4-[4-(methylsulfonyl)phenyl]-2-oxazolepropionic acid or its methyl ester.

7. A compound of claim 2 which is 4-(4-fluorophenyl)-2-(2-phenyl)ethyl-5-(4-(methylsulfonyl)phenyl)oxazole.

8. A compound of claim 2 which is 4-(4-Fluorophenyl)-2-methyl-5-methyl-5-[4-(methylsulfonyl)phenyl]oxazole.

9. A compound of claim 2 which is 4-(4-fluorophenyl)-5-[4-(methylsulfonyl)phenyl]-2-phenyloxazole.

10. A compound of claim 2 which is 2-Benzyl-4-(4-fluorophenyl)-5-(4-(methylsulfonyl)phenyloxazole.

11. A compound of claim 2 which is 4-(4-fluorophenyl)-5-[4-(methylsulfonyl)phenyl]-2-(3-phenyl)propyloxazole.

12. A compound of claim 2 which is 4-(4-fluorophenyl)-5-[4-(methylsulfonyl)phenyl]-2-propyloxazole.

13. A compound of claim 2 which is 2-(tertbutyl)-4-(4-fluorophenyl)-5-[4-(methylsulfonyl)phenyl]oxazole.

14. A compound of claim 2 which is 4-(4-fluorophenyl)-2-(4-methoxyphenyl)methyl-5-[4-(methylsulfonyl)phenyl]oxazole.

15. A compound of claim 2 which is 4-(4-fluorophenyl)-2-(3-methoxyphenyl)methyl-5-[4-(methylsulfonyl)phenyl]oxazole.

16. A compound of claim 2 which is 2-diphenylmethyl-4-(4-fluorophenyl)-5-[4-(methylsulfonyl)phenyl]oxazole.

17. A compound of claim 2 which is 4-(4-fluorophenyl)-5-[4-(methylsulfonyl)phenyl]oxazole acetic acid or its ethyl ester.

18. A compound of claim 2 which is 4-(4-fluorophenyl)-5-[4-(methylsulfonyl)phenyl]oxazolepropionic acid or its methyl ester.

19. A compound of claim 2 which is 4-(4-fluorophenyl)-5-[4-(methylsulfonyl)phenyl]oxazolebutanoic acid or its methyl ester.

20. A pharmaceutical composition for the treatment of inflammation which comprises an antiinflammatory amount of the compound of claim 1 and a pharmaceutically acceptable carrier.

21. A method of treating inflammation in a patient suffering therefrom which comprises administering a compound of claim 1 in unit dosage form.

* * * * *